United States Patent [19]

Kitaura et al.

[11] Patent Number: 5,036,088
[45] Date of Patent: Jul. 30, 1991

[54] ANTIALLERGY AND ANTIINFLAMMATORY AGENTS, COMPOSITIONS AND USE

[75] Inventors: Yoshihiko Kitaura; Fumitaka Ito; Rodney W. Stevens; Nobuko Asai, all of Aichi, Japan

[73] Assignee: Pfizer Inc., New York, N.Y.

[21] Appl. No.: 620,959

[22] Filed: Dec. 3, 1990

Related U.S. Application Data

[60] Division of Ser. No. 427,161, Oct. 25, 1989, Pat. No. 5,006,541, which is a continuation-in-part of Ser. No. 51,873, May 18, 1987, abandoned.

[30] Foreign Application Priority Data

Jun. 9, 1986 [JP] Japan .................................. 61-133470
Jun. 8, 1987 [JP] Japan .................................. 62-142779

[51] Int. Cl.$^5$ .................. C07D 235/26; C07D 263/58
[52] U.S. Cl. ..................................... 514/375; 514/387; 514/338; 548/221; 548/305; 546/270; 546/271

[58] Field of Search ................ 548/221, 305; 546/270, 546/271; 514/338, 375, 387

Primary Examiner—Mary C. Lee
Assistant Examiner—Peter Davis
Attorney, Agent, or Firm—Peter C. Richardson; J. Trevor Lumb; James M. McManus

[57] ABSTRACT

Compounds of the formula

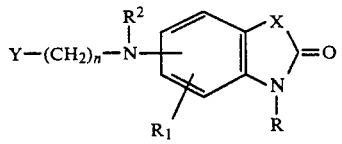

where Y is alkyl, aryl or heterocyclic, n is 1-7, R is hydrogen, alkyl, aralkyl or carboxymethyl, $R_1$ is acetoxy, thiophenoxy, hydrogen, halo, alkyl, alkoxy or trifluoromethyl, $R_2$ is hydrogen, alkyl or alkanoyl and X is C=O, $CH_2$, NH, O or S as antiallergy and antiinflammatory agents.

11 Claims, No Drawings

ANTIALLERGY AND ANTIINFLAMMATORY AGENTS, COMPOSITIONS AND USE

CROSS REFERENCE TO RELATED APPLICATIONS

This application is a divisional of application Ser. No. 07/427,161, filed 10/25/89 (now U.S. Pat. No 5,006,541), which is a continuation-in-part of application Ser. No. 51873, filed May 18, 1987 now abandoned.

BACKGROUND OF THE INVENTION

This invention relates to novel heterocyclic compounds having an alkylamino group in a side chain attached to the benzene ring wherein said alkylamine group may be further substituted by an aryl or heteroaryl containing group. Those new compounds are inhibitors of both the cyclooxygenase (CO) and lipoxygenase (LO) enzymes, and are of use in the treatment or alleviation of allergic or inflammatory conditions in mammals including human.

Arachidonic acid is known to be the biological precursor of several groups of endogenous metabolies, prostaglandins including prostacyclins, thromboxanes and leukotriences. The first step of the arachidonic acid metabolism is the release of estrified arachidonic acid and related unsaturated fatty acids from membrane phospholipids, via the action of phospholipase. Free fatty acids are then metabolized either by cyclooxygenase to produce the prostaglandins and thromboxanes or by lipoxygenase to generate hydroperoxy fatty acids which may be further converted to the leukotrienes. The prostaglandins exhibit diverse physiological effects depending upon their structure. For example, PGE and PGA inhibit gastric secretion as well as lower arterial blood pressure. The thromboxane, especially, thromboxane $A_2$ is a potent vasoconstrictor and platelet aggregatory substance. The leukotrienes are the biological source of the slow reacting substance of anaphylaxis (SRS-A), a chemical mediator in allergic bronchial asthma.

Aspirin and most other non-steroidal anti-inflammatory drugs inhibit the cyclooxygenase enzyme. Both anti-inflammatory activity and analgesic activity associated with these drugs are rationalized in terms of their inhibition on the action of cyclooxygenase. The lipoxygenase inhibiting activity of one agent, AA861 (2, 3, 5-trimethyl-6-(12-hydroxy-5.10-clodecadiynyl)-1,4-benzoquinone), is reported (see, Yoshimoto, et al., Biochim, et Biophys. 713, 470–473 (1982).) CGS-5391B (C. E. Hock et al., Prostaglandins, 28, 557–571 (1984)) has recently been known as a combination cycloxygenase and lipoxygenase inhibitor.

The determination that the compounds of this invention inhibit both cycloxygenase and lipoxygenase reflects the clinical value of these compounds in preventing proinflammatory and hypersensitivity reactions.

According to PCT Patent Application (WO 8501289) there are described and claimed a number of benzoxazolone and benzothiazolone derivatives useful for the treatment of inflammatory conditions and thrombosis.

SUMMARY OF THE INVENTION

This invention provides novel heterocyclic compounds of the formula

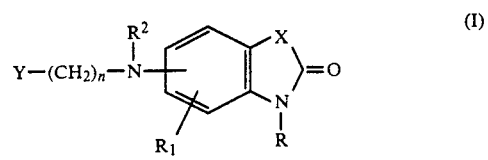

or a pharmaceutically acceptable acid addition salt thereof, wherein R is hydrogen, alkyl of one to three carbon atoms, benzyl or carboxymethyl; $R_1$ is hydrogen, acetoxy, thiophenoxy, fluoro, chloro, methoxy, methyl or trifluoromethyl; $R_2$ is hydrogen, alkyl of one to three carbon atoms, alkanoyl of one to three carbon atoms or benzyl; X is C=O, $CH_2$, NH, O or S; n is 1 to 7; and Y is styryl, thiophenoxy, methyl, phenylamino, N-methylphenylamino, N-benzylphenylamino, phenoxy, thienyl, furyl, pyridyl, phenyl, substituted phenyl wherein the substituent is dimethylamino, methyl, methoxy, flouro or chloro or disubstituted phenyl wherein said substituents are each chloro, hydroxy or methoxy with the proviso that when Y is phenoxy, thiophenoxy, phenylamino, N-methylphenylamino or N-benzylphenylamino, n is 2–7.

The pharmaceutically acceptable acid addition salts of the compounds of the formula (I) are those formed from acids which form non-toxic acid addition salts, for example, the hydrochloride, hydrobromide, sulfate or bisulfate, phosphate or acid phosphate, acetate, citrate, fumarate, gluconate, lactate, maleate, succinate, tartrate, methanesulfonate, benzene sulfonate and toluenesulfonate, formate salts.

In formula (I) the positions of substitution by the containing alkylamino group and by $R_1$ other than hydrogen are not limited but are each preferably at 4-position, 5-position and 6-position of the benzo ring, both groups being more preferably in an ortho relation to each other.

A preferred group of compounds of the present invention are those wherein X is C=0 and n is 3. Especially favored within this group is the compound where Y is phenyl and R, $R_1$ and $R_2$ are each hydrogen.

A second preferred group of compounds are those wherein X is $CH_2$ and n is 1 or 3. Especially preferred within this group are the compounds where Y is phenyl and R, $R_1$ and $R_2$ are each hydrogen.

A third group of favored compounds are those wherein X is NH, R is alkyl of one to three carbon atoms, $R_1$ is alkoxy of one to three carbon atoms and $R_2$ is hydrogen. Especially preferred are compounds where Y is styryl and n— is 0 or 2, and those where Y is phenyl and n— is 1 or 3.

A fourth group of preferred compounds are those wherein X is S and n— is 3. Especially favored is the compound where Y is phenyl and R, $R_1$ and $R_2$ are each hydrogen.

A fifth group of favored compounds are those where X is O, Y is pyridyl, styryl, methyl, phenyl, thienyl or substituted phenyl where said substituent is methyl, dimethylamino, methoxy, fluoro or chloro, R is hydrogen or alkyl of one to three carbon atoms, $R_1$ is hydrogen, fluoro, acetoxy, thiophenoxy, chloro, methoxy or methyl, and $R_2$ is hydrogen or alkyl of one to three carbon atoms. Especially preferred are compounds where Y is methyl or phenyl, R and $R_1$ are each hydrogen and n is 1, 3 or 5. Also especially favored in this group are compounds where Y is phenyl or pyridyl, R and $R^2$ are each hydrogen, n is 1, 3 or 5 and $R_1$ is methyl, methoxy, fluoro or chloro substituted at the 5-position.

Especially preferred individual compounds of this invention:

6-(3-phenylpropyl)amino-2-benzoxazolone;
6-(5-phenylpentyl)amino-2-benzoxazolone;
6-(n-heptylamino)-2-benzoxazolone;
6-N-methyl-N-(3-phenylpropyl)amino-2-benzoxazolone;
5-Fluoro-6-(3-phenylpropyl)amino-2-benzoxazolone;
5-Methyl-6-(3-phenylpropyl)amino-2-benzoxazolone;
5-Methoxy-6-(pyridin-3-ylmethyl)amino-2-benzoxazolone;
5-Methoxy-6-(pyridin-2-ylmethyl)amino-2-benzoxazolone;
5-Methoxy-6-(3-phenylpropyl)amino-2-benzoxazolone; and
6-(3-phenylpropyl)amino-2-benzothiazolone.

The present invention also includes a pharmaceutical composition comprising a pharmaceutically acceptable carrier or diluent and a compound of formula (I), and a method for treating an allergic or inflammatory condition in a mammal, especially man, which comprises administering to said mammal an antiallergy or anti-inflammatory effective amount of a compound of formula (I).

DETAILED DESCRIPTION OF THE INVENTION

The compounds of formula (I) may be prepared by a number of different routes. In one embodiment, they are prepared from an amino-substituted compound of the formula (II) according to the following reaction steps:

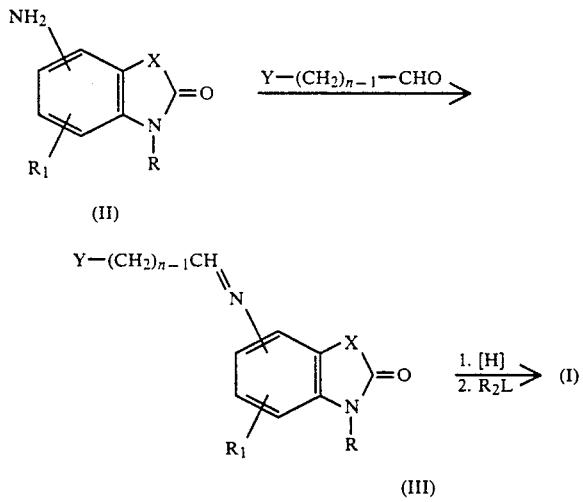

In the above formulae, X, n, R and $R_1$ are as previously defined, and L is a good leaving group. The first step involves the treatment of compound (II) with an aldehyde, $Y-(CH_2)_{n-1}-CHO$, in the presence of a dehydrating agent. The reaction is preferably conducted at ambient temperature. Higher temperatures up to 80° C. can be employed without any significant disadvantages. Suitable solvents which do not react with the reactants and/or products are, for example, benzene, toluene and tetrahydrofuran. The preferred dehydrating agent is molecular sieves, although inorganic salts such as magnesium sulfate, potassium hydrogensulfite and sodium sulfate can also be employed. When the preferred temperature is used, the reaction is substantially complete within a few hours. On completion, the product (II) can be isolated and/or purified conventionally e.g. recrystallization or chromatographing. It is, however, more convenient not to isolate this product but to subject it (i.e., in situ) to reaction conditions of the second step.

The starting materials (II) and the aldehyde $Y-(CH_2)_{n-1}-CHO$ are either known compounds or may be prepared by methods reported in the prior part references, see e.g., R. L. Clark and A. A. Pessolano, *J. Am. Chem. Soc.*, 80, 1662 (1958).

The second step involves reduction of the C=N double bond by reaction with an appropriate hydrogen source. Reduction can be carried out in a number of ways. Compounds (III) may be reduced catalystically with hydrogen. It is normally achieved with a heterogeneous catalyst such as platinum ($PtO_2$), palladium (Pd/C) or nickel in e.g. methanol or ethanol at ambient temperature. Heating is possible but is not generally necessary. Alternatively, the compounds may be reduced using a metal hydride. The hydride agents suitably employed in this reduction include sodium borohydride, sodium cyanoborohydride and lithium cyano borohydride. This reaction is conducted at ambient temperature, with an excess of the hydride agent in e.g. methanol or ethanol. Similar reduction using stannous chloride as a reducing agent can be carried out in methanol/aqueous hydrochloric acid. A preferred temperature for carrying out this is from 0° to 80° C. Reduction is ordinarily complete within a few hours. The product of formula (I) is isolated by standard methods known in the art. Compounds (I) wherein $R_2$ is other than hydrogen can be obtained by further reacting the reduced product with $R_2L$, e.g. alkylation. Purification can be achieved by conventional means, such as recrystallization or chromatographing.

In another embodiment, the compounds of formula (I) are prepared by the following process:

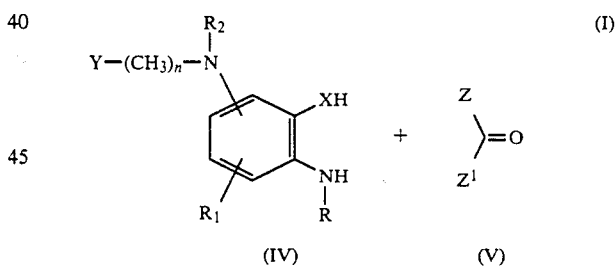

In the above formulae X, n, R, $R_1$ are as previously defined and Z and Z' are both good leaving groups.

Ring forming reaction is generally performed by contacting a compound of formula (IV) with a compound of formula (V) in a reaction-inert solvent, in the presence of a base. Representative examples of compound (V) include but not limited to, phosgene, dimethyl carbonate, diethyl carbonate, urea and N, N-carbodiimidazole. A wide variety of bases can be used in the reaction and they include organic amines, alkali metal hydroxides, alkali metal carbonate, alkali metal bicarbonates, alkali metal hydrides, alkali metal alkoxides, alkaline earth metal hydroxides, alkaline earth metal carbonates, alkaline earth metal hydrides and alkaline earth metal alkaxides. Preferred basic agents are triethylamine, sodium hydroxide, sodium ethoxide, sodium hydride, calcium hydride, potassium carbonate and sodium carbonate. Suitable reaction-inert solvents include acetone, diethyl ether, tetrahydrofuran, water, $C_1$–$C_3$ alkanol, methylene chloride, N,N-dimethylformamide, and toluene. The reaction is usually carried out in the temperature range from −20° C. to 100° C. Reaction times of from 30 minutes to a few hours are common. The product can be isolated and purified by conventional procedures, such as recrystallization or chromatography.

The pharmaceutically acceptable salts of the novel compounds of formula (I) are readily prepared by contacting said compound with a stoichiometric amount of an appropriate mineral or organic acid in either aqueous solution or in a suitable organic solvent. The salt may then be obtained by precipitation or by evaporation of the solvent. Among those enumerated earlier, especially preferred salt is the hydrochloride.

The compounds of formula (I) possess inhibiting activity on the action of the cyclooxygenase as well as on the action of the lipoxygenase. This activity has been demonstrated by a cell culture assay using rat peritoneal cavity resident cells which determines the effect of said compounds on the metabolism of arachidonic acid.

The ability of the compounds of formula (I) to inhibit both enzymes make them useful for controlling the symptoms induced by the endogenous metabolites arising from arachidonic acid in a mammalian subject. The compounds are therefore valuable in the prevention and treatment of such disease states in which the accumulation of said arachidonic acid metabolite is the causative factor, e.g., allergic bronchial asthma, skin disorders, rheumatoid arthritis, osteoarthritis, and thrombosis. Thus, these compounds are of particular use in the treatment or alleviation of allergic or inflammatory conditions in a human subject.

When a compound of the formula (I) or a pharmaceutically acceptable salt thereof is to be used as either an anti-allergic agent or an anti-inflammatory agent, it can be administered to a human subject either alone, or, preferably, in combination with pharmaceutically-acceptable carriers or diluents in a pharmaceutical composition, according to standard pharmaceutical practice. A compound can be administered by a variety of conventional routes of administration including orally, parentally and by inhalation. When the compounds are administered orally, the dose range will be from about 0.1 to 20 mg/kg body weight of the subject to be treated per day, preferably from about 0.1 to 1.0 mg/kg per day in single or divided doses. If parental administration is desired, then an effective dose will be from 0.1 to 1.0 mg/kg body weight of the subject to be treated per day. In some instances it may be necessary to use dosages outside these limits, since the dosage will necessarily vary according to the age, weight and response of the individual patient as well as the severity of the patient's symptoms and the potency of the particular compound being administered.

For oral administration, the compounds of formula (I) can be administered, for example, in the form of tablets, powders, lozenges, syrups or capsules, or as an aqueous solution or suspension. In the case of tablets for oral use, carriers which are commonly used include lactose and corn starch, and lubricating agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to make the preparation isotonic.

The present invention is illustrated by the following examples. However, it should be understood that the invention is not limited to the specific details of these examples. Proton nuclear magnetic resonance spectra (NMR) were measured at 60MHz unless otherwise indicated for solutions in perdeuterodimethyl sulfoxide (DMSO-$d_6$) and peak positions are expressed in parts per million (ppm) downfield from tetramethylsilane. The peak shapes are denoted as follows: s, singlet; d, doublet, t, triplet; q, quartet; m, multiplet; b, broad.

EXAMPLE 1

6-(3-Phenylpropyl)amino-2-benzoxazolone

To a suspension of 6-amino-2-benzoxazolone (6.00 g) and molecular sieves 4A (10.0 g) in dry benzene (100 ml) was added 3-phenylpropanal (5.25 ml), and then the mixture was stirred at room temperature for 1 hour. Methanol (150 ml) was combined with this and sodium borohydride (1.50 g) was added in portions at room temperature The reaction mixture was filtered, the filtrate was concentrated and 5% sodium bicarbonate was added. The organic material was extracted with dichloromethane. The dichloromethane phase was separated, washed with brine. Drying and removal of solvent under reduced pressure gave a crude product which was crystallized from hot ethanol to afford 7.07 g of the title compound: mp 129°–130° C.

IR (Nujiol): 3350, 3200, 1730, 1700, 1630 cm$^{-1}$.

NMR (CDCl$^3$): 1.10–2.25 (m, 2H), 2.50–4.40 (m, 3H), 6.20–7.55 (m, 8H), 8.80–9.40 (m, 1H).

EXAMPLE 2

6-(3-Phenylpropyl)amino-2-benzoxazolone Hydrochloride

A methanol solution (40 ml) containing 3.06 g of 6-(3-Phenylpropylamino)-2-benzoxazolone was combined with an ethereal solution saturated with gaseous hydrogen chloride (40 ml) at ice-bath temperature. The resulting solid was collected by filtraton, washed with ether and dried to give the title compound (3.470 g).

m.p.: 155°–158° C.

IR(Nujiol): 3230, 3020, 2600, 2450, 2360, 1780, 1740, 1630 cm$^{-1}$.

NMR: 1.70–2.30 (m, 2H), 2.50–2.90 (m, 2H), 3.00–3.50 (m, 2H), 6.90–7.60 (m, 8H), 11.60–11.90 (m, 1H).

EXAMPLE 3

6-(N-Methyl-N-3-phenylpropyl)amino-2-benzoxazolone Hydrochloride

To a mixed solution of 3M sulfuric acid (0.81 ml) and 40% aqueous formaldehyde (0.46 ml) was added dropwise a suspension of sodium borohydride (272 mg) and 6-(3-phenylpropyl)amino-2-benzoxazolone (536 mg) at −10° C. After addition, dichloroethane (30 ml) was added and the aqueous phase was made basic by addition of 5% sodium bicarbonate solution. The organic layer was separated and washed with brine. The dried solution was evaporated at reduced pressure, and the obtained residue (479 mg) was dissolved in ethanol (10 ml). To this was added an ethereal solution saturated with gaseous hydrogen chloride (30 ml). The precipitated product was recrystallized from dichloromethane-ether to give 337 mg of the title product.
m.p.: 136°-139° C.
IR(Nujiol): 3300, 2650, 2580, 2500, 1780, 1630 cm$^{-1}$
NMR: 1.50-2 20 (m, 2H), 2.40-2.90 (m, 2H), 3.15 (s, 3H), 3.30-3.80 (m, 2H), 7.00-7.90 (m, 8H).

EXAMPLE 4

3-Methyl-6-(3-Phenylpropyl)amino-2-benzoxazolone

By reaction of 6-amino-3-methyl-2-benzoxazolone with phenylpropanal using the procedure of Example 1, the title compound was prepared.
m.p.: 97°-98° C.
IR(Nujiol): 3400, 1740, 1630, 1610 cm$^{-1}$
NMR: 1.60-2.30 (m, 2H), 2.50-3.20 (m, 4H), 3.30 (s, 3H), 3.40-3.80 (m, 1H), 6.20-6.90 (m, 3H), 7.25 (s, 5H).

EXAMPLE 5

5-(3-Phenylpropyl)amino-3,3-ethylenedioxy-2-oxindole

By reaction of 5-amino-3,3-ethylenedioxy-2-oxindole with 3-phenylpropanal using the procedure of Example 1, the title compound was prepared.
m.p.: 106°-108° C.
IR(Nujiol): 3370, 3300, 1730, 1690, 1630, 1610 cm$^{-1}$
NMR: 1.75-2.20 (m, 2H), 2.50-3.75 (m, 5H), 4.20-4.80 (m, 4H), 6.30-6.85 (m, 3H), 7.00-7.70 (m, 6H).

EXAMPLE 6

5-Benzylamino-2-oxindole

By reaction of 5-amino-2-oxindole with benzaldehyde using the procedure of Example 1, the title compound was prepared.
m.p.: 203°-205.5° C.
IR(Nujiol): 3350, 1832, 1760 cm$^{-1}$
NMR: 3.25 (s, 2H), 4.16 (d, 2H, J=6 Hz), 5.72-5.85 (t, 1H), 6.39 (d, 1H, J=10 Hz), 6.60-7.08 (m, 2H), 7.28 (s, 5H), 9.50 (s, 1H).

EXAMPLE 7

5-(3-Phenylpropyl)amino-2-oxindole

By reaction of 5-amino-2-oxindole (1.48 g) with 3-phenylpropanal using the procedure of Example 1, the title compound (1.20 g) was prepared.
m.p.: 120°-122° C.
IR(Nujiol): 3350, 3150, 1680, 1600 cm$^{-1}$
NMR (CDCl$_3$) 1.40-2.20 (m, 2H), 2.75 (t, 2H, J=7 Hz), 3.10 (t, 2H, J=7 Hz), 3.45 (s, 2H), 6.20-6.80 (m, 3H), 7.20 (s, 5H), 8.75 (br.s., 1H).

EXAMPLE 8

6(3-Phenylpropyl)amino-2-benzothiazolone

By reaction of 6-amino-2-benzothiazolone (1.66 g) with 3-phenylpropanal using the procedure of Example 1, the title compound (0.82 g) was prepared.
m p.: 145°-149° C.
IR(Nujiol): 3400, 1650, 1610, 1590 cm$^{-1}$
NMR (CDCl$_3$): 1.70-2.20 (m, 2H), 2.50-3.30 (m, 4H), 4.10-4.50 (m, 1H), 6.30-7.00 (m, 3H), 7.20 (s, 5H), 10.70-11.20 (m, 1H).

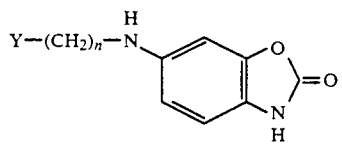

| Example No. | Y—(CH$_2$)$_n$—$\overset{H}{N}$— | Form | m.p. (°C.) | IR(cm$^{-1}$) | NMR |
|---|---|---|---|---|---|
| 9 | ![phenyl]—CH=CH—CH$_2$—$\overset{H}{N}$—<br>5 position | free | 139-141 | 3220, 1765, 1730 | 4.15 (d, 2H, J=4Hz), 5.60-5.90 (m, 1H), 6.38-6.50 (m, 3H), 6.78-7.03 (m, 1H), 7.30 (s, 8H), 12.19 (s, 1H) |
| 10 | ![phenyl]—(CH$_2$)$_3$—$\overset{H}{N}$—<br>5 position | free | 77-79 | 3420, 3150, 1750, 1620, 1610 | 1.25 (br.s., 1H), 1.60-2.20 (m, 2H), 2.75 (t, 2H, J=7Hz), 3.10 (t, 2H, J=7Hz), 6.10-6.45 (m, 2H), 6.90 (d, 1H, J=9Hz), 7.25 (s, 5H), 8.50-10.50 (m, 1H) |
| 10a | CH$_3$O—![phenyl]—(CH$_2$)$_3$$\overset{H}{N}$—<br>6 position | HCl | 248-249 | 3250, 2700, 1770, 1745 | 1.85-2.00 (m, 2H), 2.61 (t, 2H, J=7.3Hz), 3.19-3.25 (m, 2H), 3.72 (s, 3H), 6.85 (d, 2H, J=8.8Hz), 7.11 (d, 2H, J=8.8Hz), 7.18 (d, 1H, J=8.1Hz), 7.29 (d, 1H, J=8.1Hz), 7.47 (s, 1H), 11.93 (s, 1H) |

-continued

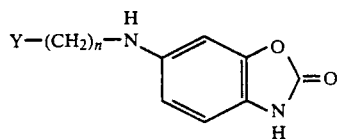

| Example No. | Y—(CH₂)ₙ—NH— | Form | m.p. (°C.) | IR(cm⁻¹) | NMR |
|---|---|---|---|---|---|
| 11 | Ph—(CH₃)₅—NH— (5 position) | free | 113–114 | 3300, 1750, 1630 | 1.20–2.00 (m, 6H), 2.40–2.80 (m, 2H), 2.85–3.30 (m, 2H), 3.40–3.90 (m, 1H), 6.10–6.50 (m, 2H), 6.95 (d, 1H, J=7Hz), 7.20 (s, 5H), 9.00–9.90 (m, 1H) |
| 12 | Ph—(CH₂)₅—NH— (6 position) | free | 115–116 | 3420, 3200, 1750, 1635 | 1.00–2.10 (m, 6H), 2.30–3.90 (m, 5H), 6.20–7.70 (m, 8H), 8.50–9.60 (m, 1H) |
| 13 | Ph—(CH₂)₅—NH— (6 position) | HCl | 153–155 | 3230, 3210, 2650, 2600, 2520, 2430, 2370, 1780, 1740, 1630 | 1.10–2.10 (m, 6H), 2.40–2.80 (m, 2H), 3.00–3.48 (m, 2H), 7.00–7.60 (m, 8H), 11.70–12.00 |
| 13a | Ph—(CH₂)₇—NH— (6 position) | free | 102–103 | Nujiol 3100, 2950, 2850, 1750 | at 270MHz 1.36–1.37 (m, 6H), 1.57–1.65 (m, 4H), 2.60 (m, 3H), 3.06 (m, 3H), 3.56 (br.s, 1H), 6.37 (dd, 1H, J=8.8, 2.2Hz), 6.50 (d, 1H, J=2.2Hz), 6.83 (d, 1H, J=8.8Hz), 7.14–7.30 (m, 5H), 8.21 (br.s., 1H) |
| 14 | Ph—CH₂—NH— (6 position) | free | 168–170 | 3350, 1830, 1760, 1720 | 4.26 (d, 2H, J=6Hz), 5.99–6.18 (t, 1H), 6.34–6.86 (m, 3H), 7.32 (s, 5H), 10.80–11.0 (m, 1H) |
| 15 | Ph—CH₂—NH— (6 position) | HCl | 185–186 | 3150, 1828, 1770 (KBr) | 4.42 (s, 2H), 7.05 (s, 1H), 7.17 7.69 (m, 7H), 8.08 (s, 1H), 11.58 (s, 1H) |
| 16 | Ph—CH₂—NH— (5 position) | free | 141–142 | 3450, 3200, 1760, 1740, 1620 | 4.25 (d, 2H, J=6Hz), 5.70–6.10 (m, 1H), 6.10–6.40 (m, 3H), 6.85 (d, 1H, J=9Hz), 7.30 (s, 5H), 10.80–11.20 (m, 1H) |
| 17 | Ph—CH=CH—CH₃—NH— (6 position) | free | 164–165.5 | 3300, 1720, 1690 | 3.76–3.94 (t, 2H), 5.68 5.88 (m, 2H), 6.35–6.89 (m, 4H), 7.33 (s, 5H), 11.00 (s, 1H) |

-continued

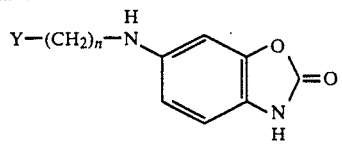

| Example No. | Y—(CH₂)ₙ—NH— | Form | m.p. (°C.) | IR(cm⁻¹) | NMR |
|---|---|---|---|---|---|
| 18 | Ph—CH—CH—CH₂—NH— (6 position) | HCl | 166–168 | 3220, 1862, 1765, 1730 | 4.05 (d, 2H, J=6Hz), 6.20–6.47 (m, 2H), 6.64 (s, 1H), 6.90–7.52 (s, 8H), 8.00 (s, 1H), 11.67 (s, 1H) |
| 19 | CH₃OOC—C₆H₄—CH₂—NH— (6 position) | free | 201–203 | 3400, 3180, 3100, 1770, 1710, 1640, 1620 | 3.83 (s, 3H), 4.33 (d, 2H, J=6Hz), 5.90–6.90 (m, 4H), 7.45 (d, 2H, J=8Hz), 7.90 (d, 2H, J=8Hz) |
| 19a | CH₃—C₆H₄—CH₂—NH— (6 position) | free | 151 dec. | 3410, 1740, 1640, (Nujiol) | at 270MHz, 2.35 (s, 3H), 4.0 (s, 1H), 4.26 (d, 2H, J=5.1Hz), 6.42 (dd, 1H, J=8.8, 2.2Hz), 6.54 (d, 1H, J=2.2Hz), 6.84 (d, 1H, J=8.8Hz), 7.14–7.30 (m, 4H). |
| 20 | CH₃—(CH₂)₆—NH— (6 position) | free | 101–103 | 3420, 3200, 1760, 1640, 1620 (Nujiol) | 0.65–2.00 (m, 13H), 2.80–3.30 (m, 2H), 3.40–3.80 (m, 1H), 6.20–6.65 (m, 2H), 6.85 (d, 1H, J=8Hz), 8.50–9.20 (m, 1H) |
| 21 | Ph—CH₂—NH— (7 position) | free | 193.5–196 | 3200, 1760, 1650 (KBr) | 3.42 (br.s, 1H), 4.42 (d, 2H, J=7Hz), 6.25–6.38 (m, 2H), 6.7–7.0 (m, 1H), 7.34 (s, 5H), 11.38 (br.s, 1H) |
| 22 | Ph—CH=CHCH₂—NH— (7 position) | free | 173.5–175 | 3320, 1750, 1640 | 4.0 (m, 2H), 5.92 (m, 1H), 6.25–6.60 (m, 4H), 6.86 (d, 1H, J=8Hz), 7.34 (s, 5H), 11.25 (br.s., 1H) |
| 23 | Ph—CH₂—CH₂—CH₂—NH— (7 position) | HCl | 181–183 | 3450, 1800, 1770 | 1.94 (m, 2H), 2.72 (t, 2H, J=7Hz), 3.22 (t, 2H, J=7Hz), 5.18 (br.s., 2H), 6.4–6.6 (m, 2H), 6.92 (d, 1H, J=9Hz), 7.25 (s, 5H), 11.45 (br.s., 1H) |
| 24 | 2-thienyl—CH₂—NH— (6 position) | free | 166–168 | 3380, 1835, 1750, 1716 | 4.42 (d, 2H, J=6Hz), 5.90–6.10 (t, 1H), 6.34–7.00 (m, 5H), 7.29 (dd, 1H), 10.93 (br.s., 1H) |
| 24a | 2-furyl—CH₂—NH— (6 position) | free | 142–144 | 3350, 3000, 1750, 1710 | at 270MHz in CDCl₃ 4.40 (s, 1H), 4.30 (s, 2H), 6.25 (s, 1H), 6.32 (s, 1H), 6.47 (d, 1H, J=8.1Hz), 6.61 (s, 1H), 6.88 (d, 1H, J=8.1Hz), 7.37 (s, 1H), 9.18 (s, 1H) |

-continued

Y—(CH$_2$)$_n$—NH—[benzoxazol-2(3H)-one]

| Example No. | Y—(CH$_2$)$_n$—NH— | Form | m.p. (°C.) | IR(cm$^{-1}$) | NMR |
|---|---|---|---|---|---|
| 24b | (pyridin-2-yl)-CH$_2$-NH— 6 position | free | 164–167 | Nujiol 3400, 1780 1710, 1640 | at 270MHz in CDCl$_3$ 4.43 (d, 2H, J=5Hz), 4.85 (s, 1H), 6.52 (dd, 1H, J= 8.1, 2.2Hz), 6.59 (d, 1H, J=2.2Hz), 6.84 (d, 1H, J=8.1Hz), 7.19–7.34 (m, 2H), 7.65–7.70 (m, 1H), 8.59 (d, 1H, J=4.4Hz) |
| 24c | (pyridin-3-yl)-CH$_2$-NH— 6 position | 2HCl | 205 (dec) | Nujiol 1760, 1630 | at 270MHz 4.51 (s, 2H), 6.54 (d, 1H, J=8.8Hz), 6.74 (s, 1H), 6.84 (d, 1H, J=8.1Hz), 7.98–8.03 (m, 1H), 8.40 (d, 1H, J=6.6Hz), 8.80 (d, 1H, J=5.1Hz), 8.88 (s, 1H), 11.30 (s, 1H) |
| 24d | (pyridin-2-yl)-CH$_2$-CH$_2$-CH$_2$-NH— 6 position | free | 170 (dec) | Nujiol 3370, 2650 1760, 1630 | at 270MHz 1.87–1.98 (m, 2H), 2.75–2.85 (m, 2H), 2.96–3.44 (m, 2H), 5.56 (d, 1H, J=5.9Hz), 6.35 (dd, 1H, J=8.1, 2.2Hz), 6.51 (d, 1H, J=2.2Hz), 6.79 (d, 1H, J=8.1Hz), 7.17–7.2 7.28 (m, 2H), 7.66–7.72 (m, 1H), 8.48 (d, 1H, J=5.1Hz), 11.02 (br.s, 1H) |
| 24e | 3,4-dichlorophenyl-(CH$_2$)$_3$-NH— 6 position | HCl | 171–172 | 3440, 1775 | 2.08 (m, 2H), 2.72 (t, 2H, J=7.3Hz), 3.23 (t, 2H, J=7.3Hz), 7.05–7.5 (m, 6H), 11.67 (s, 1H) |
| 24f | 4-HO-3-OCH$_3$-phenyl-(CH$_2$)$_3$-NH— 6 position | HCl | 154–157 | 3560, 3330 1780, 1750 | 2.05 (m, 2H), 2.62 (t, 2H, J=7.3Hz), 3.2 (t, 2H, J=7.3Hz), 3.81 (s, 3H), 6.57 (dd, 1H, J= 8.8, 2.2Hz), 6.67–6.79 (m, 2H), 7.09 (d, 1H, J= 7.8Hz), 7.28 (d, 1H, J= 7.8Hz), 7.42 (s, 1H), 11.71 (s, 1H) |
| 24g | 4-(CH$_3$)$_2$N-phenyl-(CH$_2$)$_3$-NH— 6 position | free | 143–144 | 3400, 1750 | 1.88 (m, 2H), 2.62 (t, 2H, J=7.3Hz), 2.91 (s, 6H), 3.09 (t, 2H, J= 7.3Hz), 4.4 (br.s, 1H), 6.34 (dd, 1H, J=8.8, 2.2Hz), 6.45 (s, 1H), 6.67 (d, 2H, J=10Hz), 6.77 (d, 2H, J=10Hz), 7.05 (d, 2H, J=10Hz), 10.72 (s, 1H) |
| 24h | (pyridin-4-yl)-CH$_2$-NH— 6 position | HCl | 213 (dec) | 1760, 1640 1605 | 4.62 (s, 2H), 6.42 (dd, 1H, J=8.1, 2.2Hz), 6.61 (s, 1H), 6.82 (d, 1H, J= 8.1Hz), 8.01 (d, 2H), 8.86 (d, 2H), 11.27 (s, 2H |

-continued

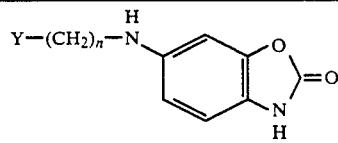

| Example No. | Y—(CH₂)$_n$—NH— | Form | m.p. (°C.) | IR(cm$^{-1}$) | NMR |
|---|---|---|---|---|---|
| 24i | phenyl-S-(CH₂)₂-NH— <br> 6 position | free | 143-144 | 3370, 1720 1690, 1630 | 3.09-3.31 (m, 4H), 5.71 (t, 1H, J=5.9Hz), 6.34 (d, 1H, J=8.8, 2.2Hz), 6.52 (d, 1H, J=1.4Hz), 6.79 (d, 1H, J=8.1Hz), 7.18-7.39 (m, 5H), 11.09 (br.s, 1H) |
| 24j | phenyl-O-(CH₂)₂-NH— <br> 6 position | free | 170-171 | 3400, 3200 1740, 1700 1635 | 3.42-3.35 (m, 2H), 4.08-4.12 (m, 2H), 5.7 (t, H, J=5.9Hz), 6.44 (dd, 1H, 8.8, 2.2Hz), 6.64 (d, 1H, J=2.2Hz), 6.81 (d, 1H, J=8.8Hz), 6.9-6.96 (m, 3H), 7.25-7.36 (m, 2H), 11.08 (s, 1H) |
| 24k | phenyl-N(CH₃)-(CH₂)-NH— <br> 6 position | free | 123-125 | 3430, 3300 1760, 1640 1610 | 2.9 (s, 3H), 3.13-3.21 (m, 2H), 3.47 (m, 2H), 5.55 (t, 1H, J=5.9Hz), 6.38 (dd, 1H, J=8.8, 2.2Hz), 6.56 (d, 1H, J=1.4Hz), 6.61 (d, 1H, J=7.3Hz), 6.7 (d, 2H, J=8.1Hz), 6.8 (d, 1H, J=8.8Hz), 7.15 (dd, 2H, J=8.8, 7.3Hz), 11.07 (br.s, 1H) |

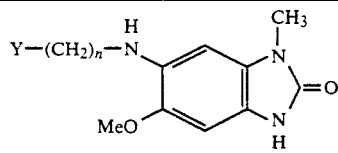

| Example No. | Y—(CH₂)$_n$—NH— | m.p. (°C.) | IR(KBr) cm$^{-1}$ | NMR ppm |
|---|---|---|---|---|
| 25 | phenyl-CH₂-NH— | 219-222 | 3100, 1685 | 3.13 (s, 3H), 3.77 (s, 3H), 4.32 (d, 2H, J=6Hz), 5.01 (t, 1H, J=6Hz), 6.32 (s, 1H), 6.57 (s, 1H), 7.2-7.5 (m, 5H), 10.29 (s, 1H) |
| 26 | phenyl-CH=CH-CH₂-NH— | 213.5-215 | 3000, 1680 | 3.2 (s, 3H), 3.78 (s, 3H), 3.92 (m, 2H), 4.72 (t, 1H, J=3Hz), 6.39 (d, 1H, J=16Hz), 6.42 (s, 1H), 6.58 (s, 1H), 6.61 (d, 1H, J=16Hz), 7.20-7.4 (m, 5H), 10.30 (br.s., 1H) |
| 27 | phenyl-CH₂-CH₂-CH₂-NH— | 182.5-184 | 3150, 1710 | 1.90 (m, 2H), 2.69 (t, 2H, J=6Hz), 3.09 (q, 2H, J=6Hz), 3.18 (s, 3H), 3.73 (s, 3H), 4.41 (t, 1H, J=3Hz), 6.26 (s, 1H), 6.55 (s, 1H), 7.14-7.30 (m, 5H), 10.26 (s, 1H) |

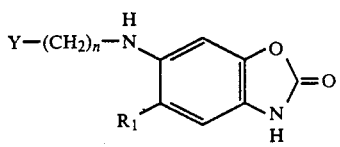

| Example No. | Y—(CH$_2$)$_n$—$\overset{H}{N}$— | R$_1$ | m.p. (°C.) | IR(Nujiol) cm$^{-1}$ | NMR (ppm) |
|---|---|---|---|---|---|
| 28 | C$_6$H$_5$—CH$_2$—CH$_2$—CH$_2$—$\overset{H}{N}$— | CH$_3$O— | 132–133 | 3480, 3200, 1790, 1730, 1635, 1600 | 1.70 (m, 2H), 2.55–3.35 (m, 4H), 3.83 (s, 3H), 4.00–4.35 (m, 1H), 6.50 (s, 1H), 6.60 (s, 1H), 7.24 (s, 5H), 9.30–9.70 (m, 1H) |
| 28a | C$_6$H$_5$—CH$_2$—$\overset{H}{N}$— | CH$_3$O— | 177–179 | 3450, 3150, 3100, 1760, 1640 | at 270MHz 3.80 (s, 3H), 4.30 (d, 2H, J=5.9Hz), 5.44 (t, 1Hz, J=5.9Hz), 6.43 (s, 1H), 6.63 (s, 1H), 7.18–7.37 (m, 5H), 11.05 (br.s, 1H) |
| 29 | C$_6$H$_5$—CH$_2$—CH$_2$—CH$_2$—$\overset{H}{N}$— | F— | 150–152 | 3400, 3200, 1760, 1730, 1645, 1620 | 1.70–2.25 (m, 2H), 2.50–3.35 (m, 4H), 3.85–4.40 (m, 1H), 6.50 (d, 1H), J=7Hz), 6.72 (d, 1H, J=10Hz), 7.20 (s, 5H) 10.50–11.10 (m, 1H) |
| 30 | C$_6$H$_5$—CH$_2$CH$_2$—CH$_2$—$\overset{H}{N}$— | CH$_3$— | 135–137 | 3400, 1750, 1640, 1620 | 1.70–2.45 (m, 2H), 2.10 (s, 3H), 2.60–3.55 (m, 4H), 6.50 (s, 1H), 6.75 (s, 1H), 7.25 (s, 5H) |
| 31 | C$_6$H$_5$—(CH$_2$)$_5$—$\overset{H}{N}$— | Cl— | 133–135 | 3450, 3150, 1760, 1640, 1610 | 1.50–4.70 (m, 7H), 6.50 (s, 1H), 6.90 (s, 1H), 7.30 (s, 5H), 10.70–11.30 (m, 1H) |
| 32 | 3-pyridyl-CH$_2$—$\overset{H}{N}$— | CH$_3$— | 190–193 | 3450, 1750, 1645, 1590, 1580 | at 270MHz 2.16 (s, 3H), 4.37 (d, 2H, J=5.9Hz), 5.53–5.58 (m, 1H), 6.42 (s, 1H), 6.76 (s, 1H), 7.30–7.74 (m, 1H), 7.75 (d, 1H, J=8.1Hz), 8.43 (d, 1H, J=2.7Hz), 8.59 (s, 1H), 10.95 (br.s, 1H) |
| 33 | C$_6$H$_5$—(CH$_2$)$_3$—$\overset{H}{N}$— | CH$_3$CO$_2$— (4-position) | 182–184 | 3380, 3200 1770, 1715 | 1.78–1.89 (m, 2H), 2.66–2.71 (m, 2H), 2.96–3.03 1635 (m, 2H), 3.84 (s, 3H), 5.86 (t, 1H, J=5.1Hz), 6.8 (d, 1H, J=2.2Hz), 6.83 (d, 1H, J=2.2Hz), 7.17–7.31 (m, 5H), 11.28 (br.s, 1H) |
| 34 | C$_6$H$_5$—(CH$_2$)$_3$—$\overset{H}{N}$— | C$_6$H$_5$—S— | 173–174 | 3150, 3050 1760, 1610 1500, 1460 1315, 1120 | 1.67–1.78 (m, 2H), 2.46 (t, 2H, J=8.1Hz), 3.08 (q, 2H, J=5.9Hz), 5.27 (t, 1H, J=5.9Hz), 6.71 (s, 1H), 7.06–7.3 (m, 1H), 11.24 (br.s, 1H) |

-continued

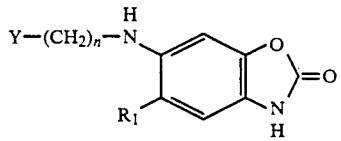

| Example No. | Y—(CH$_2$)$_n$—N(H)— | R$_1$ | m.p. (°C.) | IR(Nujiol) cm$^{-1}$ | NMR (ppm) |
|---|---|---|---|---|---|
| 35 | (phenyl)-CH$_2$-N(H)- | CH$_3$— (4-position) | 159–160 | 3450, 1750 1640 | 2.15 (s, 3H), 4.22 (d, 2H, J=6.6Hz), 6.06 (t, 1H, J=6.6Hz), 6.23 (d, 1H, J=1.5Hz), 6.33 (d, 1H, J=1.5Hz), 7.19 –7.37 (m, 5H), 11.13 (br.s, 1H) |

EXAMPLE 36

5-(3-Phenylpropyl)amino-2-benzimidazolone

By reaction of 5-amino-2-benzimidazolone with phenylpropanal using the procedure of Example 1, the title compound was prepared, m.p. 205–206° C.

IR (Nujiol): 3000, 1705 cm$^{-1}$.

NMR: 1.79–1.85 (m, 2H), 2.67 (t, 2H, J=8 Hz), 2.93 (br.s, 2H), 5.16 (s, 1H), 6.17 (d, 1H, J=8.1 Hz), 6.19 (s, 1H), 6.63 (d, 1H, J=8.1 Hz), 7.17–7.31 (m, 5H), 10.03 (s, 1H), 10.18 (s, 1H).

EXAMPLE 37

6-(N-BenzYl-N-3-phenylpropyl)amino-2-benzoxazolone

A mixture containing 6-(3-phenylpropyl)amino-2-benzoxazolone, benzyl chloride and triethylamine was heated in ethanol under reflux. Upon cooling, the solvent was removed from the mixture to give the title compound as a crude product. The product was purified by column chromatography, and further recrystallized from dichloromethane to afford an analytical sample.

m.p. 112°–114° C.

IR (Nujiol): 1755, 1640 cm$^{-1}$.

NMR: 1.92–2.03 (m, 2H), 2.62–2.68 (m, 2H), 3.36–3.41 (m, 2H), 4.48 (s, 2H), 6.39 (dd, 1H, J=8.8, 2.9 Hz), 6.53 (d, 1H, J=2.2 Hz), 6.82 (d, 1H, J=8.1 Hz), 7.16–7.33 (m, 10H), 8.90 (br.s, 1H).

EXAMPLE 38

6-(N-Acetyl-N-3-phenylpropyl)amino-2-benzoxazolone

By reaction of 6-(3-phenylpropylamino)-2-benzoxazoloe with the acetyl chloride using the procedure of Example 37, the title compound was prepared.

m.p.: 154°–155° C.

IR (Nujiol): 1850, 1780, 1620 cm$^{-1}$.

NMR: 1.81–1.87 (m, 2H), 1.87 (s, 270 MHz, 3H), 2.59–2.65 (m, 2H), 3.74–3.80 (m, 2H).

EXAMPLE 39

5-(3-(Phenylpropyl)aminoindole-2,3-dione 5-(3-Phenylpropyl)amino-3,3-ethylenedioxy-2-oxindole (420 mg) (Example 5) was heated at reflux in a mixture of concentrated hydrochloric acid (9 ml) and acetic acid (3 ml) for 1 hour. The reaction mixture was cooled to room temperature. Removal of hydrochloric acid and acetic acid under reduced pressure gave a crude product which was recrystallized from methanol - either to afford the title compound (330 mg).

m.p.: 154°–155° C.

IR Nujiol): 3220, 1730 and 1630 cm$^{-1}$.

NMR: 1.90–2.10 (m, 2H), 2.71 (t, 2H, J=8 Hz), 3.24 (t, 2H, J=8 Hz), 7.00 (d, 1H, J=8 Hz), 7.18–7.27 (m, 5H), 7.63–7.70 (m, 2H).

We claim:

1. A compound of the formula

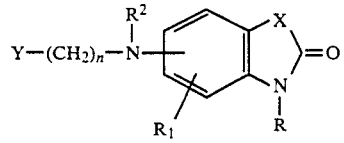

or a pharmaceutically acceptable acid addition salt thereof, wherein R is hydrogen, alkyl having one to three carbon atoms, benzyl or carboxymethyl; R$_1$ is acetoxy, thiophenoxy, hydrogen, fluoro, chloro, methoxy, methyl or trifluoromethyl; R$_2$ is hydrogen, alkyl having one to three carbon atoms, alkanoyl having one to three carbon atoms or benzyl; X is NH, or O; n is an integer of 1 to 7; and Y is styryl, methyl, N-methylphenylamino, N-benzylphenylamino, phenylamino, phenoxy, thiophenoxy, thienyl, furyl, pyridyl, phenyl, substituted phenyl wherein said substituent is methyl, dimethylamino, methoxy, fluoro or chloro, or disubstituted phenyl wherein said substituents are each chloro, hydroxy or methoxy with the proviso that when Y is phenoxy, thiophenoxy, phenylamino, N-methylphenylamino or N-benzylphenylamino n is 2-7.

2. A compound of claim 1, wherein X is NH, R is alkyl having one to three carbon atoms, R$_1$ is alkoxy having from one to three carbon atoms and R$_2$ is hydrogen.

3. A compound of claim 2, wherein n is 1 and Y is styryl.

4. A compound of claim 2, wherein n is 3 and Y is phenyl.

5. A compound of claim 2, wherein n is 1 and Y is phenyl.

6. A compound of claim 2, wherein n is 2 and Y is styryl.

7. A compound of claim 1, wherein X is O, Y is pyridyl, styryl, methyl, phenyl, thienyl or substituted phenyl wherein said substituent is methyl, dimethylamino, methoxy, fluoro or chloro; R is hydrogen or alkyl having one to three carbon atoms; R$_1$ is hydrogen, acetoxy, thiophenoxy, fluoro, chloro, methoxy or methyl; and $R_2$ is hydrogen or alkyl having one to three carbon atoms.

8. A compound of claim 7, wherein Y is methyl or phenyl, R and $R_1$ *are each hydrogen and n is* 1, 3 or 5.

9. A compound of claim 7, wherein Y is phenyl or pyridyl, R and $R_2$ *are each hydrogen, n is* 1, 3 or 5 and $R_1$ is methyl, methoxy, fluoro or chloro substituted at the 5-position.

10. A pharmaceutical composition for the treatment of allergic or inflammatory conditions in a mammal, said composition comprising an effective amount of a compound according to claim 1, with a pharmaceutically acceptable carrier.

11. A method for treating an allergic or inflammatory condition in a mammal which comprises administering to said mammal an antiallergy or anti-inflammatory effective amount of a compound according to claim 1.

* * * * *